United States Patent [19]

Shafer

[11] Patent Number: 4,698,362

[45] Date of Patent: Oct. 6, 1987

[54] LOW VISCOSITY OIL BASED PESTICIDE COMPOSITIONS

[75] Inventor: Jimmie G. Shafer, Gladstone, Mo.

[73] Assignee: Mobay Corporation, Pittsburgh, Pa.

[21] Appl. No.: 711,702

[22] Filed: Mar. 14, 1985

[51] Int. Cl.$^4$ .................... A01N 47/10; A01N 47/28; A01N 57/26
[52] U.S. Cl. ..................................... 514/490; 514/78; 514/479; 514/594
[58] Field of Search ................. 514/78, 490, 479, 478, 514/594

[56] References Cited

U.S. PATENT DOCUMENTS

| | | | |
|---|---|---|---|
| 2,006,227 | 6/1935 | Bousquet | 514/78 |
| 3,114,673 | 12/1963 | Lemin | 514/490 |
| 3,553,328 | 1/1971 | Koundakjian | 514/490 |
| 4,226,883 | 10/1980 | Yamamoto et al. | 514/479 |
| 4,237,113 | 12/1980 | Cardarelli | 514/490 |

OTHER PUBLICATIONS

Tenth Edition of the Merck Index—pp. 779 and 780.
Tenth Edition of the Merck Index—p. 64.

*Primary Examiner*—Allen J. Robinson
*Attorney, Agent, or Firm*—Gene Harsh; Lawrence S. Pope

[57] ABSTRACT

The present disclosure is concerned with a technique for producing storage stable, non-caking, low viscosity pesticidal concentrates and the compositions so obtained. The technique involves milling a solid biologically active compound in a low viscosity aliphatic petroleum fraction in which it is slightly soluble until it has an average particle size of less than about 10 microns at a temperature in excess of about 40° C. in the presence of a high or ultra-high surface area silica and lecithin. The milling is conducted in such a manner as to avoid melting any significant portion of the biologically active compound undergoing milling. The concentrate so obtained, typically display room temperature viscosities between about 20 and 2,000 cps and contain between about 120 and 480 grams per liter of biologically active compound. These compositions are more redispersible and have a lower viscosity than similar compositions with equivalent concentrations of biologically active compounds which were obtained by milling at ambient temperature. There are suitable for either direct application or application after dilution in oils or water to any large area such as agricultural fields or forests which are typically treated with pesticides or growth regulants.

17 Claims, No Drawings

LOW VISCOSITY OIL BASED PESTICIDE COMPOSITIONS

BACKGROUND OF THE INVENTION

For many years, the art has recognized the desirability of liquid formulations of biologically active compounds such as pesticides and growth regulants. However, many of the interesting biologically active compounds suitable for these end uses are solids at room temperature and are too expensive and too powerful in effect to be used in most applications without dilution with inert ingredients. Two general approaches to this problem have been developed. In one, the pesticide manufacturer or formulator dilutes the active ingredients with other solid materials in such a manner that the total formulation can then be readily dispersed into a liquid medium, usually water, by the ultimate end use or applicator. Such formulations include the wettable powders and water dispersible granules which are also known as dry flowable. The other approach has been to disperse or dissolve the active ingredient in a liquid medium in such a manner that it can either be used directly in such applications as ultra low volume spraying or can be diluted by the end user or applicator in liquid medium such as water or ecologically tolerable oils.

These liquid formulations pose the problem of stability both during the time it takes to distribute the product to the ultimate end user or applicator and also during the period between application seasons when the end user does not expend all of the purchased material during a given application season. Both solutions and dispersions can display instability but the solutions are usually more stable. They can become unstable if they are exposed to conditions such as cold temperatures which cause some of the dissolved active ingredient to precipitate. These precipitated crystals may not readily redissolve under conditions conveniently obtainable in the field. However, the major problem with the solution approach to formulations, is finding solvents for the biologically active compounds which are acceptable from both a cost and ecological viewpoint. Many organic solvents have been identified as being too hazardous to either human, animal or plant life to be the carriers or part of the carriers used to apply biologically active compounds, particularly in the fields of agriculture and forestry management where the application is over large open areas.

These concerns have been met by dispersing active ingredients in relatively inexpensive and ecologically acceptable liquid medium but this approach has problems of its own with regard to stability, viscosity and dilutability. The tendency of the solid particles of a dispersion to settle out or separate from the liquid medium in which they are dispersed can be inhibited by reducing the particle size of the dispersed material and by increasing the viscosity of the dispersion or suspension. In fact, in may cases just reducing the particle size of the dispersed material will increase the viscosity of the dispersion. However, a dispersion with too high a viscosity is not commercially acceptable because of the problems it poses in handling the material. "Liquid" formulations which can not be readily poured or pumped are decidedly unattractive to both manufacturers and end users. On the other hand, the less viscous a dispersion is, the greater tendency there is for the dispersed particles to separate from the dispersing medium.

A related concern is how "redispersible" a separated dispersion is. In general, the larger the particle size of the dispersed material, the more difficult it will be to redisperse it should any settling occur. This phenomenon, known as "caking", is generally less of a problem with the finer particle size dispersions although this may not be true with extremely fine particles in the range of about 1 micron and less.

Another concern with dispersions is that the dispersing medium not dissolve any significant portion of the dispersed material. Because there is, by definition, in a dispersion more dispersed material present than will dissolve in the dispersing medium, it is almost certain that any lowering of the temperature of the dispersion below the highest temperature to which it has been exposed, will result in some precipitation of previously dissolved material. Any significant precipitation will result in the formation of precipitated crystals that may cause significant difficulties in the further handling of the dispersion. For instance, if the dispersion is used in a spray application such crystals may cause the plugging of the spray or pumping apparatus used. However, while many liquids which are attractive as dispersing medium are poor solvents for many attractive active ingredients they are not complete non-solvents. The solution has generally been to manufacture dispersions at temperatures as close to ambient as possible. At such temperatures (around 20° C.) the solubility is usually so low that any precipitation which does occur upon exposing the dispersion to lower temperatures is not significant enough to be of concern.

This temperature constraint does pose some inconveniences for the manufacturer of dispersions. He would like to manufacture the dispersion at as high a concentration as possible and then dilute it for ultimate shipment. Such a procedure maximizes the efficiency with which the capital equipment, particularly the sand mill or other grinding equipment committed to such production, are utilized. However, as the concentration of the dispersion being produced increases so does its viscosity until the point is reached at which the dispersion can no longer be properly processed in the grinding equipment. For instance, if the viscosity of a dispersion being processed in a sand mill becomes too high the mill will be unable to provide the desired particle size reduction. Dispersions with too large a particle size are expected to display inadequate stability and caking. Raising the temperature at which the milling operation is conducted would lower the viscosity and enable the milling operation to be conducted at higher concentrations of dispersed material but it would also pose the significant danger of dissolving significant amounts of the dispersed material. Thus, elevated temperature milling has been avoided in those cases in which the dispersed material has any significant elevated temperature solubility in the dispersing medium.

Liquid pesticide formulations must generally be dilutable with liquid medium. It is economically unattractive to transport liquid pesticide formulations which have a sufficiently low active ingredient content to be directly applicable by most end users because this would involve freight costs for transporting a large amount of inert materials. Instead such formulations are typically produced with concentrations of active ingredients convenient for manufacturing, handling and storage. However, this means that the liquid formulation must be readily dilutable with materials available to the end user. Typical materials include water and oil. But dilution increases the problem of dispersion stability because it lowers the viscosity of the dispersion. In fact, in the case of the oil dilution some sepratation of the diluent oil from the pesticide concentrate has come to be accepted so long as the uniform dispersion may be readily reestablished. Thus, the problem of "caking" or the formation of nonredispersible sediments is of particular concern with regard to such dilute final formulations.

A convenient test for the degree of redispersibility has been developed which has a reasonable correlation with actual field experience. The dilute dispersion to be evaluated is placed into a number of sealed containers which are stored for various periods of time at various temperatures. Each container is evaluated by inverting it 180° and holding it in this position until the heavier material now at the top ceases to flow downward and then returning the container to its original position. The redispersibility of the dilute dispersion is evaluated by the number of such inversions which are necessary to produce a uniform dispersion after some settling has occurred.

Material which reforms a uniform mixture in 8 or less inversions has been found to be readily remixable in commercial spray equipment. For instance, such material poses no problems when used in 10,000 gallon tanks with recirculating pumps utilized in applying insecticide in forestry management. The agitation supplied by the recirculation pump and the design of the feed pipes is more than adequate to remix such materials to a uniform consistency after some separation has occurred.

An attractive oil based liquid pesticide concentrate with aminocarb as the active ingredient has been marketed for several years. It involved about 21 wt % of active ingredient, between 3 and 4 wt % of a hydrated silica having a surface area in excess of 100 square meters per gram, and about 0.5 wt % of a soy bean oil derived lecithin dispersed in an aliphatic petroleum fraction having a Saybolt Universal viscosity at 100° F. of less than about 100 seconds. The dispersed aminocarb had an average particle size less than about 10 microns. However, this product was produced by milling at temperatures less than 40° C. and as a result it was unable to provide the optimum combination of low viscosity and easy redispersibility especially after dilution in diesel oil.

SUMMARY OF THE INVENTION

The present invention is based upon the discovery that a properly formulated liquid pesticidal concentrate can be milled at elevated temperatures without impairing its storage stability or redispersibility and that, in fact, such elevated temperature milling improves the properties of the milled concentrate. Such a properly formulated pesticidal concentrate preferably includes between about 120 and 480 grams per liter of an active ingredient which is solid at temperatures in excess of 40° C. and which has significant solubility in the dispersing medium at elevated temperatures (more than about 0.5 wt % at 50° C.). It also includes lecithin, preferably between about 0.5 and 1.5 wt % especially preferred is a lecithin derived from soy bean oil. In addition, it also contains an appropriate amount of a high surface area or an ultra high surface area silica. Between about 2 and 10 wt % of silicas having surface areas between about 50 and 180 square meters per gram (which is typical of the hydrated silicas) or between about 0.2 and 1.0 wt % of silicas having a surface area in excess of 200 grams per square meter (typical of the fumed silicas) are particularly suitable. These components are dispersed in a low viscosity aliphatic petroleum fraction with those having a Saybolt Universal viscosity at 100° F. of between about 40 and 140 seconds being particularly preferred. The final composition is obtained by milling the active ingredient to a particle size less than about 10 microns at a temperature above about 40° C. without melting a significant portion of the active ingredient. A particularly preferred formulation utilizes between about 160 and 380 grams per liter of active ingredient and between about 4 and 8 wt % of a high surface area hydrated silica or between 0.4 and 0.8 wt % of a ultra high surface area fumed silica. A further preference is to utilize between about 0.3 and 1.0 wt % of the soy bean oil derived lecithin, especially one dissolved in soy bean oil. Preferred active ingredients include aminocarb and 2-chloro-N-[[[4-(trifluoromethoxy)phenyl]amino]carbonyl]benzamide.

DETAILED DESCRIPTION OF THE INVENTION

The present invention is applicable with any biologically active compound which is both a comminutable solid at temperatures above about 40° C. and soluble to a significant degree at elevated temperatures in aliphatic low viscosity petroleum fractions. The invention is of particular interest with regard to biologically active compounds which have a solubility in excess of about 0.5 wt % at 50° C. in such petroleum fractions. It can be any organic compound which has utility in controlling or regulating any biological pest or infestation. For instance, it could be an acaricide, bactericide, fungicide, insecticide, herbicide, molluscide, nematicide, rodenticide or animal or growth regulant which are hereinafter collectively referred to as pesticides. A particularly preferred insecticide is 4-(dimethylamino)-3-methylphenyl methylcarbamate known by the common name of aminocarb and a particularly preferred insect growth regulant is 2-chloro-N-[[[4-(trifluoromethoxy)phenyl]amino]carbonyl]benzamide.

The lecithin utilized in the present invention is a well known formulation ingredient for the food industry and is one of the very few dispersant compounds or emulsifiers with very good compatibility with aliphatic petroleum fractions. This is material that is available in a number of forms and from a number of different sources. However, for the purposes of this invention, it is preferred to utilize a lecithin that is derived from soy bean oil and is particularly preferred to utilize the lecithin as a solution in soy bean oil. One especially preferred form of lecithin is as a 60% solution in soy bean oil.

The silicas suitable for use in the present invention are either of high surface area or ultra high surface area. The high surface area silicas are typically hydrated silicas obtained from a chemical reaction in water while the ultra high surface area silicas are typically fumed silicas obtained by a high temperature flame hydrolysis. The hydrated silicas typically have surface areas in the range of 150 square meters per gram while the fumed silicas typically have surface areas in excess of 200 square meters per gram. However, there is some overlap between the two types of silicas so that it is possible to obtain fumed silicas with surface areas between about 50 and 400 square meters per gram. The ultra high surface area silicas (those having surface areas in excess of 200 square meters per gram) have a much more dramatic effect upon viscosity than the high surface area silicas and it is therefore preferred to use lower amounts of them. In particular, it is preferred to use between about 2 and 10 wt %, more especially between 4 and 8 wt % of a high surface area silica or between 0.2 and 1 wt % especially between about 0.4 and 0.8 wt % of an ultra high surface area silica. It is particularly preferred to use a hydrated silica having a surface area between about 140 and 160 square meters per gram.

The liquid medium used to prepare the liquid compositions of the present invention is a low viscosity aliphatic petroleum fraction. It has the ability to dissolve significant amounts of the biologically active compounds suitable for use in the present invention. The present invention is particularly of interest in those instances when the petroleum fraction used can dissolve 0.5 or more wt % of the biologically active compounds at 50° C. On the other hand, this petroleum fraction is an extremely poor ambient temperature solvent for the biologically active compounds which are suitable for use in the present invention. Typical room temperature solubilities are less than about 0.25 wt % at 20° C. These petroleum fractions preferably have a Saybolt Universal viscosities at 100° F. of between about 40 and 140 seconds. It is particularly preferred to utilize petroleum fractions having 100° F. viscosities between about 50 and 80 seconds. These petroleum fractions are preferably 90% or more unsulfonated and have densities between about 7.1 and 7.2 pounds per gallon. The preferred fractions also display a 50% distillation temperature at 10 millimeters of mercury between 400 and 450° F.

The four-component mixture of biologically active compound, high or ultra high surface area silica, lecithin and aliphatic petroleum fraction are subjected to grinding or milling in any appropriate apparatus capable of reducing the average particle size of the biologically active compound to less than about 10 microns. This size reduction may take place in several steps. For instance, the solid components, i.e., the biologically active compound and silica, may first be hammer milled and then mixed with the liquid components, i.e., the lecithin and the petroleum fraction, for feeding to a sand mill. Alternatively, all four components may be combined in intensive mixing equipment such as a ribbon blender or Lodige mill, then fed to a wet hammer or Rietz mill and then finally fed to a sand mill for one or several passes. The critical point is that the final size reduction be conducted at or above about 40° C.

The precise temperature of this size reduction is not critical. The size reduction or milling may be conducted at any temperature between about 40° C. and the temperature at which a significant amount of the biologically active compound is melted. It is important to avoid melting significant amounts of this compound because when the melted portions resolidify they will form undesirable crystals. These crystals may have adverse effects upon the viscosity and stability of the dispersion and may also cause difficulties in the handling and use of the dispersion including the plugging of pumping or spraying equipment.

The critical temperature is the temperature of the dispersion being processed. In the case of the sand mill, this temperature may be significantly higher than the temperature at which the mill is maintained or the temperature at which the dispersion is fed into the mill. Part of the frictional energy imparted by the mill is typically converted into heat energy which may increase the temperature of the dispersion undergoing treatment. However, routine experimentation will enable one skilled in the art to readily determine what operating conditions are necessary for his particular piece of milling equipment in order to maintain the temperature of the material undergoing treatment within the appropriate range.

The maximum acceptable temperature can be estimated from the melting point of the biologically active compound to be dispersed. The two are not necessarily the same, however. One the one hand, localized heating above this temperature may be acceptable if it does not result in melting of any significant amount of the compound. On the other hand, impurities in the biologically active compound may cause it to have a lower melting point than the pure compound. For example, pure aminocarb has a melting point between 93 and 94° C. but as its purity decreases from about 99% down to 92% its apparent melting point range widens and drops to between about 83 and 90° C. The 2-chloro-N-[[[4-(trichloromethoxy)phenyl]amino]carbonyl]benzamide has a melting point of approximately 195° C. thus allowing higher milling temperatures if desired.

The primary objective of the milling is to reduce the average particle size of the biologically active compound to less than about 10 microns. It is preferred to have an average particle size less than about 5 microns and it is especially preferred that no substantial portion of the particles have a size in excess of about 10 microns. This size reduction is conveniently obtained by one or more passes through a sand mill. In such a case, it is important that the viscosity of the material being processed by the mill not become so high as to impair the grinding efficiency of the mill. Thus, to some extent the maximum temperature at which the milling can be conducted without causing a significant melting of the biologically active compound determines the maximum concentration of biologically active compound. In other words, since the viscosity is generally lowered by raising the temperature it may be possible to process a higher concentration of a biologically active compound having a higher melting point.

The dispersion obtained from the grinding or milling apparatus may be packaged and shipped as is or it may be diluted. This is somewhat dependent upon the room temperature viscosity of this product. Although the elevated temperature viscosities in the mill are low enough to allow efficient grinding the obtained dispersion may have a room temperature viscosity unattractively high for packaging, shipping and handling. In general, end users or applicators want a product with a room temperature viscosity of no greater than about 2,000 cps and prefer a product with a viscosity less than about 1,000 cps. On the other hand, a product with too low of viscosity will display excessive settling and separation. The product ultimately shipped to the customer should therefore have a minimum viscosity of about 20 cps, preferably a viscosity in excess of about 50 cps.

One convenient way to maximize production efficiency and yet provide an optimum product to the field has been to mill at a higher concentration and dilute the milled product with more of the aliphatic petroleum fraction. In particular, dispersions containing between about 250 and 410 grams per liter of aminocarb can be conveniently sand milled at temperatures above about 40° C. and preferably to an average particle size of 5 microns or less and then diluted with further aliphatic petroleum fraction down to a concentration between about 130 and 230 preferably between about 150 and 210 and most preferably between about 160 and 200 grams per liter to display a room temperature viscosity of between about 50 and 200 cps, preferably less than about 100 cps. Alternatively the viscosity of milled concentrate can be adjusted to an acceptable field viscosity of between about 20 and 2000 cps, preferably between 50 and 1000 cps by dilution with the necessary amount of additional low viscosity petroleum fraction if any is required. At a concentration of 180 grams per liter, viscosities between about 100 and 600 cps measured at 20° C. and 30 rpms with a number 2 spindle are also attractive.

The liquid pesticidal concentrates of the present invention can be used as is or they may be diluted for final application. In either case, they can be used whenever it is desired to apply a biologically active compound such as a traditional "pesticide" or a growth regulant to a large area such as an agricultural field or a forest. These liquid pesticidal concentrates are particularly suited for application by spraying. The lower concentration concentrates can be applied without dilution in accordance with the technique known as ultra low volume spraying. This technique has been successfully utilized with a 180 gram per liter concentrate of aminocarb in treating some forest areas by spraying from an airplane. On the other hand, this same concentrate has been diluted with diesel oil at approximately a 1:7 ratio and then successfully sprayed on forest areas from an airplane.

Dispersions prepared according to the teachings of the present invention are expected to invariably have a lower viscosity than dispersions otherwise identical which were produced by milling at ambient temperatures. It is of course possible to obtain dispersions with equivalent viscosities by either reducing the concentration of biologically active compound or by conducting a less efficient milling or size reduction operation. In the latter case, it is expected that the dispersions will be less stable and will have an increased tendency to "cake" either in the concentrate form or after dilution for convenient end use application by spraying.

Throughout this disclosure, reference to viscosity is a reference to viscosity determined with a Brookfield LVT viscometer at about 20° to 25° C. and 30 rpm utilizing a number 2, a number 3 or a number 4 spindle depending upon the anticipated viscosity. It is believed that the measurement conditions are somewhat more important than in a typical case because the shear imparted by the viscometer can have an effect upon the dispersed particles in the dispersion undergoing measurement. However, it is also believed that viscosity measurements made under standard conditions on different dispersions are reliably comparable. In the discussion hereinabove and in the subsequent claims, references to viscosity are references to viscosity as determined in accordance with these standardized conditions.

The invention is further illustrated, but is not intended to be limited by the following examples in which all parts and percentages are by weight unless otherwise specified.

EXAMPLE I

Four pesticidal concentrates were prepared using an ambient and an elevated temperature milling. In particular, 1272 grams of aminocarb of purity in excess of 95% was hammer milled with 228 grams of a hydrated silica having a surface area of between about 140 and 160 square meters per gram and an average particle size 0.022 microns using a ⅛ inch screen. This material was spatula mixed with a uniform blend of 52.5 grams of a 60% solution of lecithin in soy bean oil and 4260 grams of an aliphatic petroleum fraction having a Saybolt Universal viscosity of between about 55 and 65 seconds.

A first portion of 400 grams of this four component mixture which was at about 4° C. was loaded into a small batch sand mill with 1091 grams of 1 mm glass beads. The mill was operated for 20 minutes with a product temperature of between 20° and 30° C. The resultant product was too viscous to separate from the grinding beads.

A second portion of 400 grams of this four component mixture was heated to 50° C. and then loaded into the same batch sand mill with 1 mm beads. The mill was operated in the same manner as before for 20 minutes except that the product temperature was maintained at between about 45 and 75° C. The resultant product had a room temperature viscosity with a number 3 spindle at 30 rpm of 2240 cps which decreased to 1556 cps after 7 days room temperature storage. It did not display the formation of any crystals after storage for two days at 20° C.

A third portion of 400 grams was treated in a manner essentially identical to that of the first portion, i.e., it was milled for 20 minutes with a product temperature of between about 15° and 20° C. The resultant product had a room temperature viscosity at 30 rpm with a number 4 spindle of 7420 cps.

A fourth portion of 400 grams was treated essentially identical to the second portion, i.e., it was milled for 20 minutes using a product temperature between about 50 and 70° C. The resultant product had a room temperature viscosity at 30 rpm with a number 3 spindle of 864 cps. The viscosity of the third portion dropped to 3356 cps after 7 days while the fourth portion had a viscosity of 684 cps after two days and was not later evaluated.

The general formulation for this work was as follows:

| Ingredient | Weight percent | Grams per liter |
|---|---|---|
| Aminocarb | 20.6 | 189.2 |
| Hydrated Silica | 3.7 | 34.1 |
| 60% Solution of Lecithin | 0.85 | 7.8 |
| Aliphatic Petroleum Fraction | 74.85 | 686.9 |

EXAMPLE II

Two pesticidal compositions were prepared using the same mill as in Example I with the same 1091 gram loading of 1 mm of glass beads but using a different formulation of the same raw materials with the addition of Barden clay as follows:

| Ingredient | Weight percent |
|---|---|
| Aminocarb | 20.6 |
| Hydrated Silica | 1.85 |
| Barden clay | 1.85 |
| 60% Solution of Lecithin | 0.85 |
| Aliphatic Petroleum Fraction | 74.85 |

424 grams of aminocarb was hammer milled with 38 grams of the silica and 38 grams of the clay. This material was spatula mixed with a uniform mixture of 1541 grams of the petroleum fraction and 17.5 grams of the silica.

A first portion was milled in a manner essentially identical to the third portion of Example I, i.e., with a product temperature between about 10° and 15° C. for twenty minutes. The resultant product had a room temperature viscosity at 30 rpm with a number 4 spindle of 8720 cps.

A second portion was milled in a manner essentially identical to the fourth portion of Example I, i.e., with a productt temperature of between about 50° and 60° C. for 20 minutes. The resultant product had a room temperature viscosity at 30 rpm with a number 3 spindle of 2436 cps.

The viscosity of the first portion dropped to about 1700 cps after 5 days but that of the second portion was at 1648 cps after 5 days and after 8 days the numbers were 1736 and 2156, respectively.

A microscopic examination of both portions revealed a maximum particle size of between 10 and 12 microns.

EXAMPLE III

The procedure of Example I was repeated using the same equipment and formulation except that a product temperature of between about 60° and 75° C. and a milling time of 40 minutes were utilized. The materials had been preheated to 50° C. before being fed to the mill. The resultant product had an initial room temperature viscosity at 30 rpm with a number 2 spindle of 290 cps which increased to 376 cps (number 3 spindle) after 7 days storage at ambient temperature. The maximum size particle seen by microscopic examination was 5 microns.

EXAMPLE IV

A more concentrated pesticidal composition was made using the raw materials and equipment of Example I using the following formulation:

| Ingredient | Weight percent | Grams per liter |
|---|---|---|
| Aminocarb | 38.43 | 378.5 |
| Hydrated silica | 6.92 | 68.2 |
| 60% solution of Lecithin | 1.58 | 15.6 |
| Aliphatic petroleum Fraction | 53.07 | 522.6 |

The procedure was essentially identical to that of Example I except that a product temperature between about 65° and 70° C. and a 40 minute milling time were utilized. The resultant product had an initial room temperature viscosity at 30 rpm with a number 3 spindle of 1200 cps which decreased to 936 on 3 days room temperature storage but increased to 1004 cps after 6 days. The largest size particle seen by microscopic examination was about 10 microns.

This work was essentially repeated except that milling time was only 10 minutes and the product temperature ranged from 43° to 70° C. The resultant product had an initial room temperature viscosity at 30 rpm with a number 4 spindle of 6740 cps which dropped to 2840 cps on 4 days room temperature storage. The largest particle seen by microscopic examination was about 12 microns. When this material was diluted by adding 5.4 grams to 73 grams of diesel oil and stored 4 days at room temperature one inversion (180°) and return was all that was required to restore uniformity.

EXAMPLE V

Example IV was repeated using an aminocarb of similar purity to that used in Example IV. The resultant product had an initial room temperature viscosity at 30 rpm with a number 4 spindle of 5980 cps which decreased to 4580 cps on 2 days ambient temperature storage.

A replication of this work with a 10 minute milling time gave a product with a room temperature viscosity at 30 rpm with a number 4 spindle of 6880 cps which decreased to 4780 cps on one day's room temperature storage.

EXAMPLE VI

The work of the second half of Example V was repeated with a slightly altered formulation. In particular, 153.2 grams of aminocarb of 96.8% purity, and 27.6 grams of the hydrated silica with a surface area of between about 140 and 160 square meters were hammer milled through a ⅛ inch screen and then spatula mixed with a uniform blend of 9.6 grams of a 60% lecithin solution in soy bean oil and 209.6 grams of the aliphatic petroleum fraction with a Saybolt Universal viscosity of between about 55 and 65 seconds. This mixture was heated to 50° C., loaded into a small batch sand mill with 1091 grams of 1 mm glass beads, and milled for 10 minutes at a product temperature between about 45° and 70° C. The resultant product had an initial room temperature viscosity at 30 rpm with a number 3 spindle of 1288 cps which decreased to 1200 cps after 4 days room temperature storage. The largest particle observed by microscopic examination was about 12 microns. However, when 13.3 ml of this material was diluted with 86.7 ml of diesel oil and stored for 4 days at ambient temperature, it required 8 inversions to restore uniformity. When compared to the second part of Example IV this illutrates that although increasing the lecithin content has a positive effect on viscosity it also has a negative effect on redispersibility.

Two replications of this work with slightly different aminocarb materials of 96.4 and 97.4% purity gave initial room temperature viscosities at 30 rpm with a number 3 spindle of 1880 and 1440 cps, respectively. The largest particle size observed by microscopic examination for both replications was about 10 microns.

The general formulation for this work was as follows:

| Ingredient | Weight percent | Grams per liter |
|---|---|---|
| Aminocarb | 38.3 | 378.5 |
| Hydrated silica | 6.9 | 68.2 |
| 60% solution of Lecithin | 2.4 | 23.8 |
| Aliphatic petroleum fraction | 52.4 | 516.4 |

EXAMPLE VII

Example VI was repeated with an aminocarb having a purity of 99.2. The material did not mill well and insufficient material was recovered for a viscosity determination.

EXAMPLE VIII

Example VI was repeated with 96.4% pure aminocarb but utilizing only 2.0 wt % of the 60% lecithin solution (in soy bean oil). The resultant product had a room temperature viscosity at 30 rpm of about 4600 cps. A comparison with Examples IV and VI indicated the following:

| Example | Weight % 60% Lecithin solution | Initial room temp. viscosity | Inversions required for diesel oil diluted 4 day old product |
|---|---|---|---|
| IV | 1.6 | 6700 cps | 1 |
| VI | 2.4 | 1300 cps | 8 |
| VIII | 2.0 | 4600 cps | — |

EXAMPLE IX

The following formulation was produced on a continuous sand mill:

| Ingredient | Weight percent | Grams per liter |
|---|---|---|
| 97.5% pure aminocarb | 32.8 | 316 |
| Hydrated Silica (140–160 m²/g) | 5.9 | 57 |
| 60% Lecithin solution in soy bean oil | 1.36 | 13.1 |
| Aliphatic Petroleum fraction (100° F. SUS about 60) | 59.94 | 576.8 |

The following four step procedure was utilized:

(1) Mix 1500 g of the petroleum fraction with 32.5 g of the lecithin solution until uniform and then charge with 820 g of the aminocarb and 147.5 g of the silica to a one gallon waring blender. After mixing for 1 minute at high speed the mixture had a viscosity at ambient temperature and 30 rpm with a number 2 spindle of 110 cps.

(2) Feed the blender contents to a Rietz or wet hammer mill with screen with 0.012 inch square apertures. The treated mixture had a viscosity under standard conditions of 280 cps. Approximately 0.1 wt % was retained on a 60 mesh screen and 8.1 wt % on a 200 mesh screen.

(3) Heat the Rietz milled slurry to between 50° and 60° C. and feed to a one liter capacity sand mill which is 70% by volume filled with 2 mm beads at a rate of 80 ml/minute. The mill was operated to maintain the product temperature as it emerged from the mill at between about 50° and 60° C. The milled material had a viscosity under standard conditions of 1720 cps. Approximately 0.006 wt % was retained on a 200 mesh screen and 0.005 wt % on a 325 mesh screen.

(4) Remill the recovered product under the identical conditions. The remilled material had an initial viscosity under standard conditions of 4200 cps which dropped to 2040 cps after 3 days ambient temperature storage. About 0.008 wt % of this material was retained on a 325 mesh screen.

EXAMPLE X

The procedure of Example IX was essentially repeated except that the product temperature emerging from the mill varied between about 40° and 60° C. The following formulation richer in aminocarb and lecithin was used:

| Ingredient | Weight percent | Grams per liter |
|---|---|---|
| Aminocarb | 38.3 | 378.5 |
| Silica | 6.9 | 68.2 |
| 60% lecithin solution | 2.4 | 23.8 |
| Aliphatic petroleum fraction | 52.4 | 516.4 |

After the first sand mill pass the viscosity was 710 cps under standard conditions and after the second pass it was 420 cps. The twice milled material showed 0.007 wt % retention on a 200 mesh screen and 0.001 wt % retention on a 325 mesh screen. It was milled a third time at a 40 ml/minute feed rate and then had a viscosity under standard conditions of 550 cps which dropped to 480 cps after one day storage at ambient temperature. On microscopic examination the largest particle size observed was 18 microns.

Some of the trice milled material was diluted with an equal volume of the aliphatic petroleum fraction to give a material having a viscosity under standard conditions of 40 cps.

Both the original material and the diluted material were mixed with a diesel oil diluent commonly used in forestry spraying. In the former case, 13.3 ml were added to 86.7 ml of the oil and in the latter case 27 ml were added to 73 ml of the oil. Both mixtures required 21 inversions to restore uniformity after 24 hours storage at ambient temperature.

EXAMPLE XI

The procedure of Example IX was essentially repeated with the same formulation except that the feed rate was increased to 160 ml/minute. The viscosity after the first sand mill pass was 450 cps and after the second pass it was 780 cps, both measured under standard conditions of 20° C. and 30 rpm, with a number 3 spindle.

Some of this material was then diluted in a ratio of 62.8 parts of the petroleum fraction to 37.2 parts of milled material. This diluted material had a fairly constant viscosity of between about 40 and 80 cps on ambient temperature storage over a period of 4 months and it formed only a trace to slight soft sediment after storage for 57 days at 40° C. When this diluted material was further diluted with diesel oil at ratios of 31 and 39 parts to 69 and 61 parts of oil, respectively, and stored for four weeks at ambient temperatures it required 5 and 3 inversions, respectively, to restore uniformity.

The full strength material had a viscosity of 540 cps under standard conditions after storage for 4 months at 20° C. and became thick and agglomerated after 46 days storage at 40° C. When diluted at ratios of 23 parts and 19 parts to 77 parts and 81 parts, respectively, of diesel oil diluent it required 7 and 5 inversions, respectively, to restore uniformity after one week at ambient temperature.

EXAMPLE XII

Commercial production of in excess of 50,000 gallons of the formulation of Example IX was undertaken in accordance with the following procedure:

(1) all the ingredients were blended in a Lodige or ribbon mill.

(2) The blend was then treated in a Rietz or wet hammer mill with a 0.012 inch square aperture screen.

(3) The hammer milled material was then fed to a sand mill 70% volume loaded with 2 mm glass beads at a volume rate equivalent to four times the total internal volume of the mill per hour (4 Mill Factor or MF) and then refed to the mill under the same conditions for a second pass. The material was preheated to between about 40° and 60° C. before being fed to the mill and it was maintained at this temperature during milling.

The initial room temperature viscosity of these materials ranged from between 1000 and 16,900 cps but the viscosities after storage at 20° C. for between 10 and 135 hours ranged between about 900 and 7000 cps. There did not appear to be any correlation between aging time and viscosity except that sometimes a dramatic decrease between the initial viscosity at the least 10 hour viscosity was observed. Studies on selected batches for periods of as long as 8 weeks showed only a small effect on viscosity. While the first 7 of 33 batches displayed a wide variation in even aged viscosity ranging from about 900 and 7,600 cps the viscosity after aging between 7 and 24 hours at ambient temperature for the next 11 batches was generally between about 1,000 and 2,000 cps. It was concluded that the initial viscosities were unreliable because of an uncontrolled amount of aeration which dissipates rapidly and because of the relaxation of the milled material. Thus, even small differences in the time between sampling and testing could have caused substantial differences in observed values. It was also concluded that the aged values observed for the first 7 batches were not representative of the process because thereafter the aged values became much more consistent. It was presumed that some unrecorded variables were responsible for the wide variation in these first 7 batches. A composite sample was made of random samples drawn from the 9th, 16th, 25th and 32nd samples. Its room temperature viscosity at 30 rpm with a number 3 spindle remained between about 1010 and 1060 cps over a period of five weeks storage at 20° C. It was ultimately concluded that a room temperature viscosity at 30 rpm of between 1000 and 2000 cps was representative of the process.

This composite sample was tested for storage stability at ambient, elevated (40° C.) and depressed (−5° C.) temperatures both as combined and as diluted with various diluents. As combined it was stable under the most adverse condition of 40° C. displaying only a trace of soft sediment after 3 months. A similar result was observed for cycling from −5° C. to ambient to 40° C. for 2 months. A dilution of 18 parts of the composite with 82 parts of a diesel oil typically used for forestry spraying could be restored to uniformity after storage at 40° C. for 1 and 2 months by 6 and 9 inversions, respectively. A dilution of 16 parts of the composite, 1.3 parts of a combined anionic/nonionic surfactant and 83 parts of water could be restored to uniformity after storage at 40° C. for 1 and 2 months by 1 and 2 inversions, respectively.

EXAMPLE XIII

The material produced in Example XII was diluted with more of the low viscosity aliphatic petroleum fraction at a ratio of 6 parts by volume to 4 parts by volume of the petroleum fraction. The initial room temperature viscosity for the 33 batches varied from 70 to 276 cps while the viscosity after aging at 20° C. for between 8 and 120 hours ranged from 76 to 130 cps. Aging of samples of randomly selected batches indicates that aging for up to 8 weeks at 20° C. had a relatively insignificant effect on viscosity. Samples of all 33 batches successfully withstood two months storage at 40°.

A composite sample was prepared from random samples of the first 5 batches and tested for stability as combined and as diluted with various diluents. No objectionable sediment was observed after 3 months at 40° C. and after 2 months of cycling from −5° C. to 20° C. to 40° C. A dilution of 29 parts of the composite to 71 parts of a diesel oil diluent used in forestry spraying required 6 inversions to restore uniformity after 4 months storage at 40° C., 8 inversions after 4 months at 20° C. and 10 inversions after 4 months at −5° C. After 8 months at 20° C., 10 inversions were required and after 8 months at −5° C. 17 inversions were required. A dilution of 25 parts of the composite, 1.3 parts of a combined anionic/nonionic surfactant and 74 parts of water required only 1 inversion after storage for either 4 months at 40° C. or 8 months at 20° C. Two months storage at −5° C. required 7 inversions and 8 months required 13 inversions.

COMPARATITVE EXAMPLE I

Commercial production in accordance with Example XII using the formulation of Example IX had been done the year before that of Example XII but using a sand milling temperature well below 40° C. This material had then been diluted in accordance with the teachings of Example XIII, i.e., diluted at a ratio of 60 parts to 40 parts aliphatic petroleum fraction diluent. Initial room temperature viscosities of this material ranged from about 1200 to about 3500 cps at 30 rpm with a number 2 spindle. Samples aged from one day to two months at 20° C. displayed viscosities at the same test conditions of 860 to 2500 cps.

Dilution of 11 parts of this material with 72 parts of a diesel oil diluent used for forestry spraying could be restored to uniformity with 1 inversion after storage for as long as three weeks.

Thus, it was concluded that although this process yielded redispersible product it was at best 800% more viscous than the same formulation subject to the higher temperature milling procedure of the present invention.

COMPARATIVE EXAMPLE II

The commercial production in accordance with Example XII had also been done the previous year using a formulation similar to that of Example IV which was approximately as follows:

| Ingredient | Grams per liter |
|---|---|
| 97.4% pure aminocarb | 360 |
| hydrated silica with a 140–160 m$^2$/g surface | 68.2 |
| 60% solution of lecithin in soy bean oil | 15.6 |
| aliphatic petroleum fraction with 55–60 SUS at 100° F. | 522 | but with a sand milling temperature like that of Comparison Example I, i.e., well below 40° C.

The resultant product had a room temperature initial viscosity at 30 rpm with a number 4 spindle of between about 9300 and 13,400 cps.

The product was mixed with an equal volume of the aliphatic petroleum fraction to yield a product having initial room temperature viscosities at 30 rpm with a number 2 spindle of between about 150 and 300 cps. A dilution of 11 parts of this product with 72 parts of a diesel oil diluent used in forestry spraying required between 8 and 13 inversions to restore uniformity after 2 weeks storage at ambient temperature (about 20° C).

It was concluded that this material had inferior redispersibility because of inadequate size reduction in the sand mill. It was assumed that the very high viscosities observed before the dilution with additional petroleum fraction impaired the grinding efficiency of the sand mill. The low viscosity after this dilution was also attributed to inadequate particle size reduction.

Thus, a material of low viscosity was obtained but at the cost of poor dispersibility and stability. Storage at 40° C. for up to four weeks also indicated an inferior storage stability, also an indication of inadequate particle size reduction.

Some material obtained from this production which used an aminocarb of 95.5% purity displayed a room temperature viscosity of 735 cps after dilution with an equal volume of the aliphatic petroleum fraction. This diluted material required only 5 inversions after 2 weeks storage at room temperature in the 11 parts to 72 parts diesel oil dilution. It was concluded that this material had undergone a more thorough particle size reduction and therefore it displayed properties more typical of ambient temperature milled product.

EXAMPLE XIV

Example XII was repeated except that the aminocarb was replaced by 250 grams per liter of 2-chloro-N-[[[4-(trifluoromethoxy)phenyl]amino]carbonyl]benzamide, an insect growth regulant. The same procedure was repeated with the same formulation except that the sand milling temperature was about room temperature. The room temperature viscosities after one day storage at room temperature were as follows:

|  | 1st Sand Mill Pass | 2nd Sand Mill Pass | 3rd Sand Mill Pass |
|---|---|---|---|
| Elevated Temp. Milling (#3 Spindle, 30 rpm) | 1856 cps | 2480 cps | 2716 cps 6600 (#4, spindle, 12 rpm) |
| Ambient Temp. Milling (#4 spindle, 12 rpm) | 12250 cps | 14500 cps | 14500 cps |

The third pass was, of course, a slight deviation from the procedure of Example XII.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of pesticide concentrates which are storage stable, non-caking and of low viscosity which comprises milling an insecticidally effective amount of a solid insecticidally active compound selected from the group consisting of aminocarb and 2-chloro-N-[[[4-(trifluoromethoxyl)phenyl]amino]carbonyl]benzamide in a low viscosity aliphatic petroleum fraction in which it is slightly soluble until it has an average particle size of less than about 10 microns at a temperature in excess of about 40° C. in the presence of a high or ultra high surface area silica and lecithin without melting any significant portion of said compound.

2. A process for the production of a storage stable, non-caking, low viscosity pesticide concentrate which comprises
   (a) milling a solid insecticidally active compound selected from the group consisting of aminocarb and 2-chloro-N-[[[4-(trifluoromethoxy)phenyl]amino]carbonyl]benzamide in a low viscosity aliphatic petroleum fraction in which it is slightly soluble until it has an average particle size of less than about 10 microns at a temperature of about 40° C. or higher and at a concentration between about 250 and 410 grams per liter in the presence of high or ultra high surface area silica and lecithin without melting any significant portion of the compound, and
   (b) diluting the milled product with more of the low viscosity aliphatic petroleum fraction to obtain a concentration of insecticidally active compound of between about 130 and 230 grams per liter.

3. The process of claim 2 wherein the concentrate has a final room temperature viscosity at 30 rpm of between about 50 and 100 cps.

4. The process of claim 3 wherein the final concentration of insecticidally active compound is between about 150 and 210 grams per liter.

5. The product of the process of claim 2.

6. The product of the process of claim 3.

7. The product of the process of claim 4.

8. A process for the production of a storage stable, non-caking, low viscosity pesticide concentrate which comprises
   (a) milling a solid insecticidally active compound selected from the group consisting of aminocarb and 2-chloro-N-[[[4-(trifluoromethoxy)phenyl]amino]carbonyl]benzamide in a low viscosity aliphatic petroleum fraction in which it is slightly soluble until it has an average particle size of less than about 10 microns at a temperature of about 40° C. or higher and at a concentration between about 250 and 410 grams per liter in the presence of high or ultra high surface area silica and lecithin without melting any significant portion of the compound, and
   (b) diluting the milled product with as much of the low viscosity aliphatic petroleum fraction as necessary to obtain a final room temperature viscosity at 30 rpm of between about 20 and 2000 cps.

9. The process of claim 8 wherein the final viscosity is between about 50 and 1000 cps.

10. The process of claim 8 wherein the final concentration of the insecticidally active compound is between about 250 and 410 grams per liter.

11. The process of claim 8, 9, or 10 wherein the insecticidally active compound is aminocarb.

12. The process of claim 8, 9 or 10 wherein the insecticidally active compound is 2-chloro-N-[[[4-(trifluoromethoxyl) phenyl]amino]carbonyl]benzamide.

13. The product of the process of claim 8.

14. The product of the process of claim 9.

15. The product of the process of claim 10.

16. The product of the process of claim 11.

17. The product of the process of claim 12.

* * * * *